(12) United States Patent
Laun et al.

(10) Patent No.: US 8,132,445 B2
(45) Date of Patent: Mar. 13, 2012

(54) RHEOMETER

(75) Inventors: Martin Laun, Mannheim (DE); Jürgen Pfister, Speyer (DE); Rene Lochtman, Mannheim (DE); Günter Oetter, Frankenthal (DE); Claus Gabriel, Griesheim (DE)

(73) Assignee: BASF SE, Ludwigshafen (DE)

( * ) Notice: Subject to any disclaimer, the term of this patent is extended or adjusted under 35 U.S.C. 154(b) by 425 days.

(21) Appl. No.: 12/438,017

(22) PCT Filed: Aug. 16, 2007

(86) PCT No.: PCT/EP2007/058500
§ 371 (c)(1),
(2), (4) Date: Feb. 19, 2009

(87) PCT Pub. No.: WO2008/022960
PCT Pub. Date: Feb. 28, 2008

(65) Prior Publication Data
US 2011/0030454 A1 Feb. 10, 2011

(30) Foreign Application Priority Data

Aug. 23, 2006 (EP) .................................. 06119405

(51) Int. Cl.
*G01N 11/14* (2006.01)
(52) U.S. Cl. ...................................... 73/54.28
(58) Field of Classification Search .................. None
See application file for complete search history.

(56) References Cited

U.S. PATENT DOCUMENTS

| 4,501,155 A | 2/1985 | Garritano |
| 5,547,049 A | 8/1996 | Weiss et al. |
| 6,167,752 B1 | 1/2001 | Raffer |
| 6,240,770 B1 | 6/2001 | Raffer |
| 6,499,336 B1 | 12/2002 | Raffer |
| 6,571,610 B1 | 6/2003 | Raffer |
| 7,275,419 B2 | 10/2007 | Raffer |
| 2001/0015095 A1 | 8/2001 | Konaka |

(Continued)

FOREIGN PATENT DOCUMENTS

AT 404192 B 9/1998
(Continued)

OTHER PUBLICATIONS

Genc, S., and Phule, P.P., "Rheological properties of magnetorheological fluids," Smart Materials and Structures, 2002, vol. 11, pp. 140-146.

(Continued)

*Primary Examiner* — Hezron E Williams
*Assistant Examiner* — Alex Devito
(74) *Attorney, Agent, or Firm* — Connolly Bove Lodge & Hutz LLP

(57) ABSTRACT

The invention relates to a rheometer having a rotatable shaft (1) on which a rotor plate (2) is fastened, and having a measuring instrument (10) for measuring torques exerted on the rotor plate (2) by a substance (6) to be studied during rotation of the shaft (1), a first measurement gap (5) for holding the substance (6) to be studied being formed between a first side (3) of the rotor plate (2) and a first shear face (4) and a second measurement gap (9) for holding the substance (6) to be studied being formed between a second side (7) of the rotor plate (2), opposite the first side, and a second shear face (8). The rheometer contains a magnet for generating a magnetic field in the first and second measurement gaps (5, 9).

12 Claims, 1 Drawing Sheet

U.S. PATENT DOCUMENTS

2002/0148283 A1    10/2002    Chang

FOREIGN PATENT DOCUMENTS

| | | |
|---|---|---|
| AT | 19911441 A1 | 9/2000 |
| AT | 409304 B | 7/2002 |
| AT | 409422 B | 8/2002 |
| AT | 500358 A1 | 12/2005 |
| DE | 3423873 A1 | 1/1985 |
| EP | 1016806 B1 | 4/2003 |
| EP | 1025373 B1 | 4/2005 |

OTHER PUBLICATIONS

John, S., et al., "Magneto-rheological fluids exploiting nanometer sized particles," Proceedings of SPIE, 2002, vol. 4699, pp. 473-484.

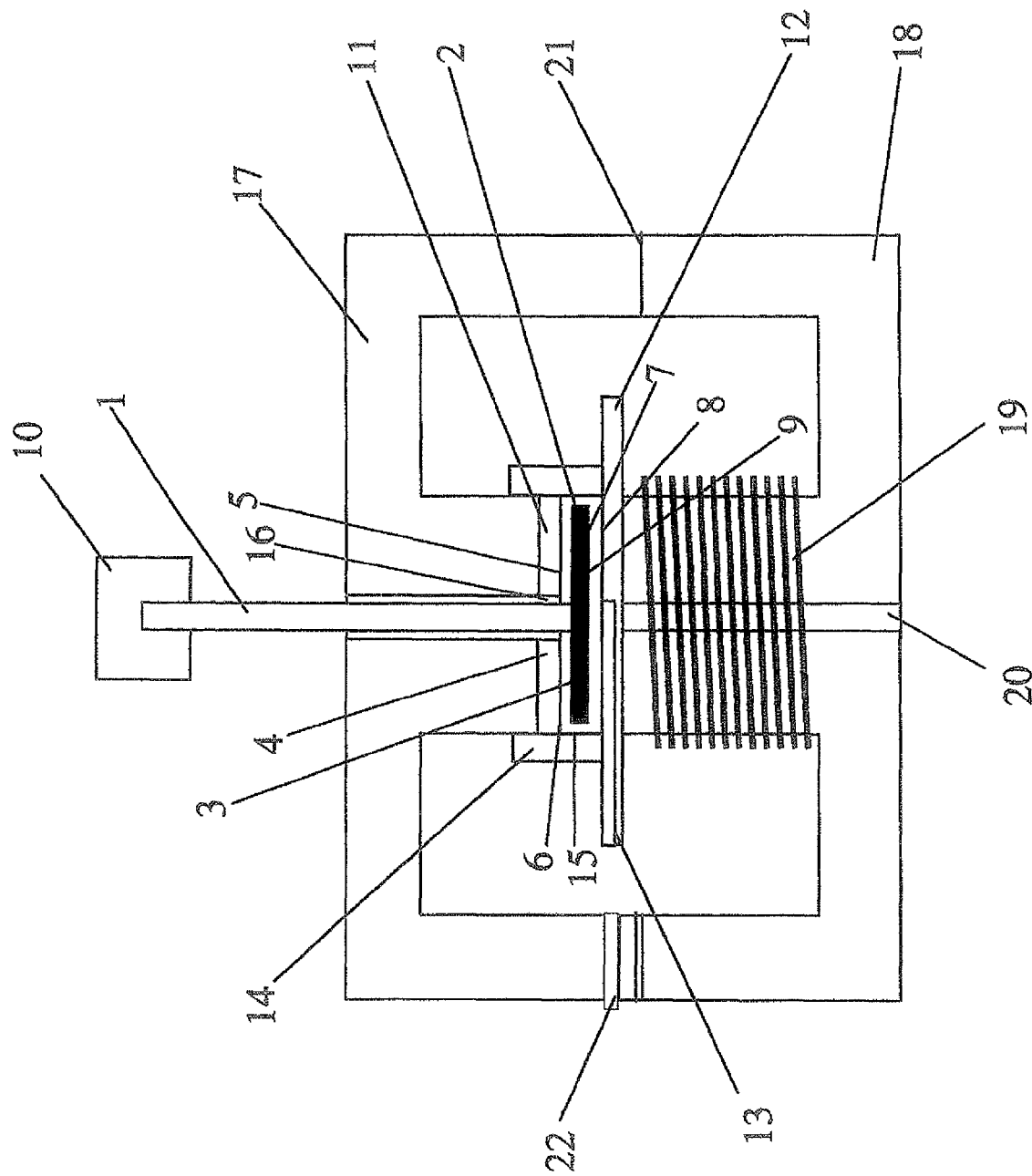

RHEOMETER

RELATED APPLICATIONS

This application is a national stage application (under 35 U.S.C. §371) of PCT/EP2007/058500, filed Aug. 16, 2007, which claims benefit of European application 06119405.6, filed Aug. 23, 2006.

The present invention relates to a rheometer having a rotor plate fastened on a rotatable shaft and to a method for determining rheological properties of a substance to be studied using a rheometer.

Rheology is the science which deals with flow processes, i.e. with the progressive deformation of a material under the effect of external forces. The deformation in the case of flow (viscous deformation) takes place at a finite rate. In real materials, plastic and elastic behavior are superimposed on the viscous behavior. Various rheometers are used according to the prior art in order to measure rheological quantities. Distinction is to be made between rotation rheometers, capillary rheometers, extension rheometers and constriction rheometers.

Rotation rheometers are most widespread in the laboratory. Three different measuring systems with various geometries are generally used in this case. These different measuring systems comprise cone/plate measuring systems, plate/plate measuring systems and cylinder measuring systems.

DE 199 11 441 A1 relates to a rotation viscosimeter having a cylinder measuring system, in which a measuring cylinder rotates in a cylindrical measuring beaker filled with the sample to be studied. The forces which the sample exerts on the measuring cylinder are then measured and evaluated, the sample filling the gap between the measuring cylinder and the measuring beaker.

DE 3423873 A1, AT 404192 B, AT 409304 B, AT 409422 B and AT 500358 A1 relate to plate-plate or cone-plate measuring systems, in which a sample is sheared between two plates aligned mutually parallel, one of which rotates.

Rotation rheometers known in the prior art according to the plate-cone or plate-plate principle, with two mutually rotating measuring faces, usually contain a stand or frame on which a plate is arranged. A rotatable shaft driven by a motor carries a rotor plate as a measurement body, which can be set in rotation by the motor via the shaft. A measuring instrument is provided, which measures for example the torque on the shaft or the moment exerted on the rotor plate by the substance to be studied, for example indirectly by measuring the electrical consumption of the motor configured as an electric motor. The measuring instrument may furthermore measure the rotation position and rotation speed of the shaft (for example by means of an angle encoder). A guide bearing for the shaft is usually formed on the stand, for which an air bearing, a magnetic bearing or another low-friction bearing arrangement is for example used. In the case of an air bearing, under axial loading of the shaft by a normal force, an air cushion counters this load similarly as a spring. Such a normal force, which is generated for example by expansion of the substance to be studied during heating or other effects during the measurement, acts on the rotor plate and therefore on the shaft. In the rheometers known in the prior art, however, an upper limit is placed on the permissible normal force by the configuration of the bearing, for example the air bearing, so that the measuring range of the rheometer is thereby restricted.

It is an object of the present invention to avoid the disadvantages of the prior art, and in particular to provide a rheometer and a method for determining rheological properties of a substance to be studied, so that a large measuring range can be covered.

This object is achieved according to the invention by a rheometer having a rotatable shaft on which a rotor plate is fastened, and having a measuring instrument for measuring torques exerted on the rotor plate by a substance to be studied during rotation of the shaft, a first measurement gap for holding the substance to be studied being formed between a first side of the rotor plate and a first shear face and a second measurement gap for holding the substance to be studied being formed between a second side of the rotor plate, opposite the first side, and a second shear face, and the rheometer containing a magnet for generating a magnetic field in the first and second measurement gaps (5, 9).

A rheometer is a device for determining rheological properties of a substance to be studied, in particular the viscosity of the substance to be studied. The rheometer according to the invention is a rotation rheometer, which operates similarly to the plate-plate and/or the cone-plate principle. A rotor plate is fastened on a rotatable shaft and is driven by a motor, for example by a laboratory stirrer.

In order to determine the rheological properties of the substance to be studied, the rheometer according to the invention comprises at least one measuring instrument, in particular a measuring instrument for measuring torques exerted on the rotor plate by the substance to be studied during rotation of the shaft. In order to determine the rheological properties of a substance to be studied (in particular a sample liquid), it is possible to make the shaft rotate at a constant rotation speed and measure the torque required for this. It is nevertheless also possible to apply a constant torque to the shaft using the motor, and to measure the rotation speed or rotation position resulting from the torque exerted on the rotor plate. The shaft may furthermore execute a sinusoidal rotation movement or a rotation movement corresponding to another waveform (oscillation experiment), in which case the elastic component of the substance to be studied can also be determined besides the viscous part. In each case, the torque which the substance to be studied exerts on the rotor plate during the latter's movement is measured (optionally indirectly) by the measuring instrument.

During a measurement, the rotor plate is in contact on both sides with the substance to be studied. The substance lies in the two measurement gaps, which are respectively bounded by one side of the rotor plate and a stationary shear face. Preferably, the measurement gaps are substantially designed symmetrically and/or both measurement gaps have the same height, which is determined by the distance between the surface of the rotor plate and the respective shear face.

The invention furthermore relates to a method for determining rheological properties of a substance to be studied, preferably a magnetorheological fluid. This method comprises the rotation of a rotor plate fastened on a shaft, the rotor plate being in contact on a first side with the magnetorheological fluid to be studied, contained in a first measurement gap, and being in contact on a second side opposite the first side with the magnetorheological fluid to be studied, contained in a second measurement gap. The method furthermore comprises the generation of a magnetic field in the first and second measurement gaps and the measurement of torques exerted on the rotor plate by the magnetorheological fluid during the rotation of the rotor plate.

The double gap measuring arrangement of the rheometer according to the invention and of the method according to the invention has the advantage that it leads to compensation for the normal forces on the rotor plate, in particular to compensation for the normal forces generated by a magnetorheological fluid in a magnetic field owing to its anisotropy, so that this no longer limits the measuring range of the rheometer as in the case of the conventional single gap. Correct fitting of the rotor plate can furthermore be checked in the rheometer according to the invention by measuring the normal force of the double gap arrangement on the shaft of the rheometer, so that the normal forces are (substantially) compensated for with correct fitting.

The rheometer according to the invention, or a rheometer intended for the method according to the invention, furthermore contains at least one magnet for generating a magnetic field extending perpendicularly to the shear plane in the first and the second measurement gap. This arrangement is used in particular to determine the rheological properties of magnetorheological fluids.

Magnetorheological fluids (abbreviation: MRF) refers in general to liquids which change their rheological properties under the effect of a magnetic field. They are usually suspensions of ferromagnetic, superparamagnetic or paramagnetic particles in a carrier liquid (often referred to as a base oil).

If such a suspension is exposed to a magnetic field, then its flow resistance increases. This is due to the fact that the dispersed magnetizable particles, for example iron powder, form chain-like structures parallel to the magnetic field lines because of their magnetic interaction. These structures are partially destroyed during the deformation of an MRF, but they reform. The rheological properties of a magnetorheological fluid in a magnetic field resemble the properties of a plastic body with a yield point, i.e. at least a minimum shear stress must be applied in order to make the magnetorheological fluid flow.

Magnetorheological fluids belong to the group of non-Newtonian fluids. The viscosity depends greatly on the imposed shear rate. The reversible viscosity change by imposing a magnetic field can take place within milliseconds.

The rheological behavior of a magnetorheological fluid can be described approximately by a Bingham model, the yield point of which rises with an increasing magnetic field strength. For example, shear stress values of a few tens of thousands of $N/m^2$ can be achieved with magnetic flux densities of less than one tesla. High transmissible shear stresses are required for the use of magnetorheological fluids in devices such as shock absorbers, clutches, brakes and other controllable equipment (for example haptic devices, crash absorbers, steer-by-wire guiding systems, gear- and brake-by-wire systems, seals, holding systems, prostheses, fitness equipment or bearings).

Known applications of magnetorheological fluids are described, for example in U.S. Pat. No. 5,547,049, in EP 1 016 806 B1 or in EP 1 025 373 B1. The rheometer according to the invention with the magnet, like the method according to the invention with the possible step of generating a magnetic field in the measurement gaps while carrying out the measurements, can therefore be used to determine the rheological properties of magnetorheological fluids. When a magnetorheological fluid is studied in a rotation rheometer with a measurement gap, the magnetorheological fluid in the magnetic field generates normal forces in the longitudinal direction (parallel to the shaft of the rheometer) owing to its anisotropy. The double gap arrangement of the present invention is therefore particularly advantageous for studying the rheological properties of magnetorheological fluids, since normal force compensation is achieved by the magnetorheological fluid-filled measurement gaps arranged on both sides of the rotor plate.

A magnetic field which is symmetrical and homogeneous is preferably generated in the two measurement gaps in order to determine the rheological properties of magnetorheological fluids. Such a symmetrical magnetic field is preferably symmetrical with respect to the rotatable shaft of the rheometer as a symmetry axis and with respect to the rotor plate as a symmetry plane.

According to a preferred embodiment of the present invention, the magnet is an electromagnet having a coil, a first magnet yoke arranged above the first measurement gap and a second magnet yoke arranged below the second measurement gap, the first and second magnet yokes being designed symmetrically with respect to the rotor plate and with respect to the shaft. A symmetrical structure of the yoke above and below with respect to the rotor plate in the double gap makes it possible to set up a uniform magnetic flux density in both measurement gaps, even in the event of the variation in the gap height or the properties of the magnetorheological fluid to be studied. A permanent magnet may nevertheless also be used for the present invention.

According to a preferred embodiment of the present invention, the rotor plate is made at least partially of a magnetizable material. A magnetizable rotor plate (for example made of the steel type with the material number 1.0037) on a shaft made of a non-magnetizable material significantly amplifies the magnetic flux density in the measurement gaps and improves the radial homogeneity of the field over the active measurement gaps. It is nevertheless also possible to use a rotor plate made of a non-magnetizable material for the rheometer according to the invention.

The two shear faces adjacent to the measurement gaps are preferably formed by a first and a second plate respectively adjacent to the first or second measurement gap, or each by a surface of the magnet (for example of the magnet yoke) which is adjacent to the first or second measurement gap.

In the rheometer according to the invention, at least one channel for holding at least one measuring sensor, selected from the group Hall probe or temperature sensor, is preferably contained in components adjacent to the measurement gaps. By means of a Hall probe, the effective magnetic flux density in the measurement gaps can be measured online. For example, the Hall probe lies in a flat channel inside a nonmagnetic plate below or above one of the measurement gaps. It is also possible to carry out the measurement using the Hall probe during the shearing of the substance to be studied in the measurement gaps, so that the magnetization change of the substance due to the shear can be recorded. Varying the radial position of the Hall probe in the channel (perpendicularly to the rotatable shaft) makes it possible to measure the radial flux density profile.

By means of the temperature sensor, in particular a thermocouple fitted as close as possible to one of the measurement gaps, the temperature of the substance to be studied in the measurement gaps can be measured online. For example, the temperature sensor lies in a flat channel inside a thermally conductive plate below or above one of the measurement gaps. It is also possible to carry out the measurement using the temperature sensor during the shearing of the substance to be studied in the measurement gaps, so that temperature changes of the substance during the shearing can be recorded, and the temperature may optionally be regulated using a temperature controller provided for this purpose.

For example, (liquid) temperature control may be provided for the middle parts of the upper and lower yoke of a magnet, which is used to generate a magnetic field in the measurement gaps. The temperature controller should as far as possible be in direct contact with the measurement gaps, in order to ensure a maximally constant temperature in both measurement gaps even in the event of a high energy input (high torque/high rotation speed). According to an alternative embodiment, the temperature controller is constructed so that the entire measuring cell of the rheometer, which comprises a housing with the rotor plate, the measurement gaps, at least a part of the shaft and optionally a magnet, is immersed in a thermally regulated liquid during a measurement and/or during the shearing.

According to a preferred embodiment of the present invention, the first and the second measurement gap are closed outward by a delimiting element. This has the advantage that the substance to be studied cannot emerge radially out of the measurement gaps because of centrifugal forces during the rotation of the rotor plate. The delimiting element may be designed in one piece or a plurality of pieces. It may be arranged directly adjacent to the rotor plate circumference (without hindering the rotation) or at a particular distance from the rotor plate circumference, so that the substance to be studied is in contact along the rotor plate circumference in both measurement gaps. The delimiting element may, for example, be an annular sleeve which concentrically encloses a circular rotor plate. Since the volume of the substance to be studied in the measurement gaps may change, an escape volume into which the substance can escape is preferably provided (for example along the shaft).

The rotor plate of the rheometer according to the invention is preferably designed circularly and has a radius in a range of preferably between 3 mm and 10 cm, particularly preferably between 5 mm and 25 mm. The rotor plate preferably comprises two plane, one plane and one conical or two conical plate surfaces. The rheometer according to the invention may furthermore comprise two shear faces, which are formed by two plane, one plane and one conical or two conical plate surfaces.

Two plane rotor plate surfaces together with two plane shear faces of the rheometer give a double plate-plate arrangement. In the plate-plate system, the substance to be studied is sheared in the measurement gaps between the rotor plate surfaces and shear faces which are aligned mutually parallel. The shear rate is in this case not the same throughout the respective measurement gap. Rather, it increases with the radius and reaches its maximum at the outer edge of the rotor plate.

Two conical rotor plate surfaces together with two plane shear faces of the rheometer give a double cone-plate arrangement, as do two plane rotor plate surfaces together with two conical shear faces of the rheometer. In the cone-plate system, a respective cone (rotor plate surface) in each case rotates over a plate (shear face). The substance to be studied lies in the measurement gap respectively arranged between them. The circumferential speed increases outward on the cone surface. At the same time, the gap height increases because of the cone shape. The effect of this is that the shear rate remains radially constant. In the present invention, therefore, the double cone arrangement makes it possible to set a uniform shear rate in the two measurement gaps.

The height of the two measurement gaps in the present invention preferably lies in the range of respectively between 0.1 and 1 mm, particularly preferably respectively between 0.2 and 0.4 mm. The measurement gap height in the rheometer according to the invention can be adjusted by selecting a particular rotor plate thickness. The rotor plate is therefore preferably replaceable in the rheometer according to the invention. With smaller gap heights, the maximally achievable shear rate is increased.

The method according to the invention may be carried out with a rheometer according to the invention. According to a preferred embodiment of the method according to the invention, the torque profile or the profile of the rotation speed on the shaft is measured continuously during the rotation of the rotor plate and the shear generated thereby. According to a further embodiment, phases alternately take place in which the rotation of the rotor plate is used exclusively to homogenize, condition or continuously load the substance to be studied, and phases in which a measurement of the torques or rotation speeds takes place during the movement (for example rotation or oscillation) of the rotor plate.

The method according to the invention may also be carried out without a magnetic field or may comprise the step of generating a (preferably homogeneous and symmetrical) magnetic field in the measurement gaps.

According to a preferred embodiment of the present invention, the method according to the invention and/or the rheometer according to the invention are used to study the suitability of a magnetorheological fluid for particular applications, in particular for its suitability to be used in an MRF clutch. The invention relates inter alia to the use of a rheometer according to the invention for the metrological characterization of a magnetorheological fluid, a dispersion or a polymer melt or solution. Besides magnetorheological fluids, for example, the double gap measuring arrangement according to the invention may also be used for measurements on viscoelastic polymer melts (polystyrene, polyamide, polybutylene terephthalate, polyoxymethylene, polyethylene, polypropylene, polyisobutylene, polydimethylsiloxane, etc.) as well as polymer solutions and dispersions, in particular polymer dispersions (styrene dispersions, acrylate copolymer dispersions etc.) or suspensions at high shear rates. For example, a substance to be studied may be sheared with shear rates of between 0.01 and $10^4$ 1/s by using the rheometer or method according to the invention. For example, shear stresses of between 0.01 and 200 kPa are then achieved. Closing the measurement gap edges by means of a delimiting element, it is possible to avoid fracture processes in the material such as at the open edge of a conventional single gap. Furthermore, this prevents the substance to be studied from being spun out of the measurement gaps by high centrifugal forces. In order to study thermoplastics, the measurement gaps may be filled by inserting disks and/or rings of the thermoplastic to be studied. The measurement gaps may, for example, be filled with magnetorheological fluids, solutions or dispersions through a filling channel intended for this purpose, while a vent channel is open. Both channels are subsequently closed in order to carry out the rheological study of the substance to be studied.

Besides studying liquids, it is also possible to carry out measurements on powders. Thus, for example materials used in magnetic powder clutches can be studied. A suitable material therefore is for example carbonyl iron powder.

EXAMPLE

A commercially available Physica MRD180(1T) measuring device from Anton Paar, Austria was modified and used in an MCR 501 rheometer from Anton Paar (0.3 Nm maximal torque). Two different rotor plates have been used. One rotor plate had a radius of 8 mm, the other a radius of 9.7 mm. Thus, in combination with the used delimiting element having a diameter of 20 mm, annular gaps of 2 mm and 0.3 mm, respectively, resulted. The rotor plate having the radius of 8 mm is used in case the torque limit of the rheometer is met during the measurement with the bigger rotor plate having the radius of 9.7 mm. With a gap height of 0.3 mm each for the two measurement gaps, a shear rate range of from 0.01 to 10,000 1/s could be covered by increase of the rotational speed of the motor, and shear stresses of between 3 Pa and 150,000 Pa could be measured. A shear rate of 10,000 1/s is achieved with the possible maximum rotational speed of 3,000 rpm in combination with the inventive measuring setup. At a rotational speed of the motor of 2,055 rpm, a radius of the rotor plate of 9.7 mm and a height of the measurement gap of 0.3 mm, a shear rate of 7000 1/s is achieved. By using a magnetizable rotor plate made of steel (material number 1.0037), the magnetic flux density with a sample (magnetorheological fluid) ranged from 0 T to 1.4 T. Measurements have been carried out in a temperature range of between −25° C. and 100° C. This rheometer according to the invention therefore had the advantage that high shear rates and a magnetic field of high magnetic flux density were achieved, without the normal forces exceeding the permissible range of the air bearing (60 N). Said measurement range could not be covered with rheometers of the prior art.

DRAWING

The invention will be explained in more detail below with the aid of the drawing, in which:

FIG. 1 shows a schematic representation of a rheometer according to the invention with a double measurement gap in section.

The rheometer comprises a rotatable shaft 1 made of a non-magnetizable material (for example austenitic stainless steel—for example material number 1.4571). The rotatable shaft 1 is connected to a motor (not shown) which drives the shaft 1. It is preferably mounted using an air bearing (not shown). A rotor plate 2, which is made of a magnetizable material (for example steel—for example material number 1.0037) is fastened on the end of the shaft 1. A first measurement gap 5, in which a substance 6 to be studied (for example a magnetorheological fluid) is contained in FIG. 1, is arranged between the upper side of the rotor plate 2 (first side 3) and a first shear face 4. A second measurement gap 9, which likewise contains the substance 6 to be studied, is formed between the lower side of the rotor plate 2 (second side 7) and a second shear face 8.

The rheometer furthermore comprises a measuring instrument 10 which measures the rotation speed and the torque of the motor, and therefore inter alia indirectly records the torque exerted on the rotor plate 2 by the substance 6 to be studied during the rotation of the shaft 1.

The first and the second shear face 4, 8 are respectively formed by a first plate 11 adjacent to the first measurement gap 5 and a second plate 12 adjacent to the second measurement gap 9. The plates 11 and 12 can be replaced, for example in order to test the effect of a material or a surface structure on the transmissible shear stress. A channel 13, which may for example hold a Hall probe or a thermocouple, is formed in the second plate 12. The two plates 11, 12 may contain further channels (not shown).

In this embodiment, the rotor plate 2 comprises two plane plate surfaces on its two sides 3, 7. This is therefore a double plate-plate arrangement.

The two measurement gaps 5, 9 are closed outward by a common delimiting element 14 in the form of a sleeve. A transition region 15, via which the substance to be studied can pass from one to the other of the measurement gaps 5, 9, extends along the delimiting element 14. So that the substance 6 has the opportunity to escape in case of a volume increase, there is an open escape region 16 around the shaft 1.

The rheometer furthermore contains a magnet for generating a magnetic field in the first and second measurement gaps. The magnet comprises an upper first magnet yoke 17, a lower second magnet yoke 18 and a coil 19. The first and the second magnet yoke 17, 18 are substantially designed symmetrically with respect to the rotor plate 2 and with respect to the shaft 1. The first yoke 17 is composed of two half segments (not shown) and the second yoke 18 is formed in one piece. Both yokes 17, 18 contain a central bore 20, which in the case of the first magnet yoke 17 receives the shaft 1. The two magnet yokes 17, 18 are assembled along the line 21. The first magnet yoke 17 contains a passage 22 through which, for example, a Hall probe to be introduced into the channel 13 or a thermocouple can be fed from outside into the interior of the magnet yoke.

The method according to the invention for determining rheological properties of a substance to be studied can be carried out with the rheometer according to the invention as represented in FIG. 1.

LIST OF REFERENCES 1 rotatable shaft
2 rotor plate
3 first side
4 first shear face
5 first measurement gap
6 substance to be studied
7 second side
8 second shear face
9 second measurement gap
10 measuring instrument
11 first plate
12 second plate
13 channel
14 delimiting element
15 transition region
16 escape region
17 first magnet yoke
18 second magnet yoke
19 coil
20 central bore
21 line between yokes
22 passage

We claim:

1. A rheometer having a rotatable shaft (1) on which a rotor plate (2) is fastened, and having a measuring instrument (10) for measuring torques exerted on the rotor plate (2) by a substance (6) to be studied during rotation of the shaft (1), wherein a first measurement gap (5) for holding the substance (6) to be studied is formed between a first side (3) of the rotor plate (2) and a first shear face (4) and a second measurement gap (9) for holding the substance (6) to be studied is formed between a second side (7) of the rotor plate (2), opposite the first side, and a second shear face (8), and wherein the rheometer contains a magnet for generating a homogeneous magnetic field in the first and second measurement gaps (5, 9).

2. The rheometer according to claim 1, wherein the magnet is an electromagnet.

3. The rheometer according to claim 1, wherein the rotor plate (2) is made at least partially of a magnetizable material.

4. The rheometer according to claim 1, wherein the magnet is an electromagnet having a coil (19), a first magnet yoke (17) arranged above the first measurement gap (5) and a second magnet yoke (18) arranged below the second measurement gap (9), the first and second magnet yokes (17, 18)

being designed symmetrically with respect to the rotor plate (2) and with respect to the shaft (1).

5. The rheometer according to claim 1, wherein the first and second shear faces (4, 8) are formed by a first and a second plate (11, 12) respectively adjacent to the first or second measurement gap (5, 9), or each by a surface of the magnet which is adjacent to the first or second measurement gap (5, 9).

6. The rheometer according to claim 1, wherein at least one channel (13) for holding at least one measuring sensor, selected from the group Hall probe or temperature sensor, is contained in components adjacent to the measurement gaps (5, 9).

7. The rheometer according to claim 1, wherein the first and the second measurement gap (5, 9) are closed outward by a delimiting element (14).

8. The rheometer according to claim 1, wherein the rotor plate (2) comprises two plane, one plane and one conical or two conical plate surfaces.

9. A method for determining rheological properties of a magnetorheological fluid to be studied, comprising rotation of a rotor plate fastened on a shaft, the rotor plate being in contact on a first side with the magnetorheological fluid to be studied, contained in a first measurement gap, and being in contact on a second side opposite the first side with the magnetorheological fluid to be studied, contained in a second measurement gap, generation of a homogeneous magnetic field in the first and second measurement gaps and measurement of torques exerted on the rotor plate by the magnetorheological fluid during the rotation of the rotor plate.

10. The rheometer according to claim 1, wherein the magnetic field is symmetrical in the first and second measurement gaps.

11. The rheometer according to claim 10, wherein the magnetic field is symmetrical with respect to the rotor plate as a symmetry plane.

12. The rheometer according to claim 10, wherein the magnetic field is symmetrical with respect to the rotatable shaft as a symmetry axis.

* * * * *